(12) United States Patent
Paul et al.

(10) Patent No.: US 9,694,213 B2
(45) Date of Patent: Jul. 4, 2017

(54) ACOUSTIC COUPLING FOR ASSESSMENT AND ABLATION PROCEDURES

(75) Inventors: Saurav Paul, Minneapolis, MN (US); Troy T. Tegg, Elk River, MN (US); Reed R. Heimbecher, Hamel, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 819 days.

(21) Appl. No.: 12/979,475

(22) Filed: Dec. 28, 2010

(65) Prior Publication Data

US 2011/0160584 A1 Jun. 30, 2011

Related U.S. Application Data

(60) Provisional application No. 61/291,778, filed on Dec. 31, 2009.

(51) Int. Cl.
*A61B 8/00* (2006.01)
*A61N 7/02* (2006.01)
*A61B 8/08* (2006.01)
*A61B 8/12* (2006.01)
*A61B 17/00* (2006.01)

(52) U.S. Cl.
CPC ............ *A61N 7/022* (2013.01); *A61B 8/0883* (2013.01); *A61B 8/12* (2013.01); *A61B 8/445* (2013.01); *A61B 8/4494* (2013.01); *A61B 2017/00106* (2013.01)

(58) Field of Classification Search
USPC ....... 600/423, 424, 433, 434, 437, 466, 462, 600/463
See application file for complete search history.

(56) References Cited

U.S. PATENT DOCUMENTS

| 6,200,268 B1 * | 3/2001 | Vince et al. ................. 600/443 |
| 6,475,151 B2 * | 11/2002 | Koger et al. ................. 600/459 |
| 6,546,276 B1 * | 4/2003 | Zanelli ........................ 600/424 |
| 7,488,289 B2 * | 2/2009 | Suorsa et al. ................ 600/466 |
| 2003/0055360 A1 * | 3/2003 | Zeleznik et al. ............. 600/587 |
| 2003/0208123 A1 * | 11/2003 | Panescu ....................... 600/431 |
| 2005/0119568 A1 * | 6/2005 | Salcudean et al. .......... 600/437 |
| 2006/0173321 A1 * | 8/2006 | Kubota et al. ............... 600/439 |

(Continued)

OTHER PUBLICATIONS

Margolis, Robert H. et al., "Wideband Reflectance Tympanometry in Chinchillas and Humans", Journal of Acoustics Society of America, pp. 1453-1464, Sep. 2001.

*Primary Examiner* — Amanda Lauritzen Moher
*Assistant Examiner* — Shahdeep Mohammed
(74) *Attorney, Agent, or Firm* — Dykema Gossett PLLC

(57) ABSTRACT

Acoustic coupling systems and methods are disclosed as these can be used for assessment and ablation procedures. An exemplary acoustic assessment system for a catheter has a flexible catheter shaft. At least one acoustic transducer is positioned in the flexible catheter shaft. The at least one acoustic transducer emits a generated acoustic signal for reflection by adjacent tissue. The at least one acoustic transducer receives a reflected acoustic signal from the adjacent tissue and generates electrical signals corresponding to one or more property of the tissue. An output device is electrically connected to the at least one acoustic transducer. The output device receives the electrical signals and generate output for a user for assessing the tissue.

20 Claims, 13 Drawing Sheets

(56) References Cited

U.S. PATENT DOCUMENTS

| | | | |
|---|---|---|---|
| 2009/0036774 A1* | 2/2009 | Weng et al. | 600/439 |
| 2010/0168570 A1* | 7/2010 | Sliwa et al. | 600/439 |
| 2010/0217160 A1* | 8/2010 | Saguchi et al. | 601/2 |
| 2010/0280390 A1* | 11/2010 | Hendriks et al. | 600/467 |

* cited by examiner

ACOUSTIC COUPLING FOR ASSESSMENT AND ABLATION PROCEDURES

CROSS-REFERENCE TO RELATED APPLICATIONS

This application claims the benefit of U.S. provisional application No. 61/291,778, filed 31 Dec. 2009 (the '778 application). The '778 application is hereby incorporated by reference as though fully set forth herein.

BACKGROUND OF THE INVENTION a. Field of the Invention

The instant invention is directed toward a catheter and a method for using the catheter for assessment and ablation procedures. In particular, the catheter of the present invention may comprise one or more acoustic transducers for assessment of tissue and/or for assessment of catheter contact with the tissue and/or for tissue ablation procedures.

b. Background Art

It is well known that benefits can be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, lesions can be formed at specific locations in cardiac tissue via coagulation necrosis to lessen or eliminate undesirable atrial fibrillation.

Several difficulties can be encountered, however, when attempting to form lesions at specific locations using some existing ablation electrodes. One such difficulty encountered with existing ablation catheters is how to assess the tissue and catheter contact with the tissue. These assessments are not readily determined using conventional fluoroscopy techniques. Instead, the physician assesses the tissue based on his/her experience using the catheter. Such experience only comes with time, and can be quickly lost if the physician does not use the catheter on a regular basis. In addition, when forming lesions in a heart, the beating of the heart further complicates matters, making it difficult to assess and maintain sufficient contact pressure between the catheter and the tissue for a sufficient length of time to form a desired lesion. If the contact between the catheter and the tissue cannot be properly maintained, a quality lesion is unlikely to be created. Likewise, timely feedback assessment and if the lesion cannot be accurately and timely assessed during formation for assessing the tissue and lesion formation is critical to forming quality lesions.

BRIEF SUMMARY OF THE INVENTION

It is desirable to be able to assess tissue characteristics, assess catheter contact with the tissue, including contact with a moving surface (e.g., the heart wall), and, optionally perform tissue ablation procedures. During use, an acoustic transducer outputs an acoustic signal, which can be reflected at least in part by tissue or surrounding anatomical structures or fabricated barrier structures. The reflected energy is received by the acoustic transducer and converted to electrical energy indicative of various tissue properties, including tissue depth and other characteristics of the tissue, and lesion formation. The inventive techniques described, depicted, and claimed herein can be employed with conventional ablation electrodes delivering diverse types of ablation energy. Alternatively, the acoustic energy itself can be used to energize the tissue and raise the temperature of the tissue, thereby forming an ablative lesion.

Acoustic coupling systems and methods are disclosed as these can be used for assessment and ablation procedures. An exemplary acoustic assessment system for a catheter may comprise a flexible catheter shaft. At least one acoustic transducer is coupled directly or indirectly to the flexible catheter shaft (e.g., to a distal end portion, to a tip portion, to or adjacent to an electrode used for sensing or ablating, embedded in an ablating element). The at least one acoustic transducer emits a generated acoustic signal for reflection by adjacent tissue. The at least one acoustic transducer receives a reflected acoustic signal from the adjacent tissue and generates electrical signals corresponding to one or more properties of the tissue. An output device is electrically connected to the at least one acoustic transducer. The output device receives the electrical signals and generates output for a user for assessing the tissue.

In exemplary embodiments, a plurality of acoustic transducer elements are configured as one of the following: a one-dimension array, a two-dimension array, a three-dimensional array, a geometric shape, a sphere, and a cylinder. Also in exemplary embodiments, an acoustic transducer is configured to generate a canceling effect of acoustic energy at a desired distance to reduce or eliminate damage to surrounding tissue or anatomical structures.

In other exemplary embodiments, the system may further comprise a shielding device or fabricated barrier structure(s) to generate a canceling effect of acoustic energy at a desired distance to reduce or eliminate damage to surrounding tissue or anatomical structures. The shielding device can be positionable within or adjacent to an anatomical structure. For example, the shielding device can be insertable into or outside of the heart (e.g., endocardially or into the pericardial space) or esophagus (e.g., via the oral cavity or via one or more minimally invasive surgical incisions, "MIS" herein). In one example, the shielding device can be cylinder-shaped or spatula-shaped to facilitate use within or adjacent to the heart or esophagus. The shielding device can be relatively rigid or flexible and/or porous e.g., sponge-like). Expandable and collapsible structures are also contemplated for use with the present invention apparatus and methods. Of course more than one shielding device can be deployed, via catheter delivery and/or MIS, during a procedure. The shielding device could also be a 'hybrid structure' that focuses or cancels energy in one region and merely blocks or deflects energy from another region. For example, a flat bottomed bowl-shaped structure or a partially flat-sided cylinder or half-pipe could accomplish both for energy impinging on either opposing major surface as could a spatula-like cannula. Therefore, as used herein, the term 'shielding device' means one or more structures configured for insertion into a body, such as a chamber of a heart, a pericardial space, an esophagus, or into position near or on organs or target or non-target tissue within the thoracic cavity that at least one [or both] of reflecting applied energy (e.g., causes a desired cancellation or focus of energy) and deflecting or blocking the energy from reaching non-target tissue.

An exemplary method comprises emitting acoustic signals from a catheter; receiving reflected acoustic signals at the catheter; and assessing tissue characteristics based on the received acoustic signals. Emitting and receiving the acoustic signals can be accomplished simultaneously or by alternating these functions.

In another embodiment, a system for assessing catheter-tissue contact may comprise means for emitting acoustic signals from a catheter. The system may also comprise means for receiving reflected acoustic signals at the catheter. The system may also comprise means for comparing the emitted and received acoustic signals. The system may also comprise means for outputting data for assessing tissue based on the received acoustic signals.

Also disclosed are systems and methods for determining a level of contact between a catheter and tissue based on the acoustic signals. Other assessments may include determining tissue properties including, for example, the following: tissue depth, number of tissue layers, tissue interfaces, and tissue type. Also disclosed are systems and methods and devices for generating a canceling effect of acoustic energy at a desired distance to reduce or eliminate damage to surrounding tissue or anatomical structures. Although the systems and methods may utilize the acoustic energy for assessment purposes (e.g., when acoustic energy transmitters are used with conventional ablation electrodes), the acoustic energy may also be delivered to the tissue for lesion formation. In exemplary embodiments, the acoustic energy can be focused for lesion formation at a predetermined tissue depth.

Output can be stored in a memory structure and/or conveyed to the user in near real-time (e.g., at a display device or other interface) so that the user can properly position the catheter on the target tissue with the desired level of contact for the ablation procedure. For example, the user may increase contact pressure if the output indicates insufficient contact. Or, for example, the user may reduce contact pressure if the output indicates too much contact. Also, the user can be provided with, for example, a map of the tissue and/or surrounding anatomical structures to facilitate determining the position of the catheter relative to the tissue or surrounding anatomical structures. The user may also be provided with ablation formation information, e.g., indicating whether a sufficient ablative lesion has been formed.

The foregoing and other aspects, features, details, utilities, and advantages of the present invention will be apparent from reading the following description and claims, and from reviewing the accompanying drawings.

DETAILED DESCRIPTION OF THE INVENTION

Figure 1A:
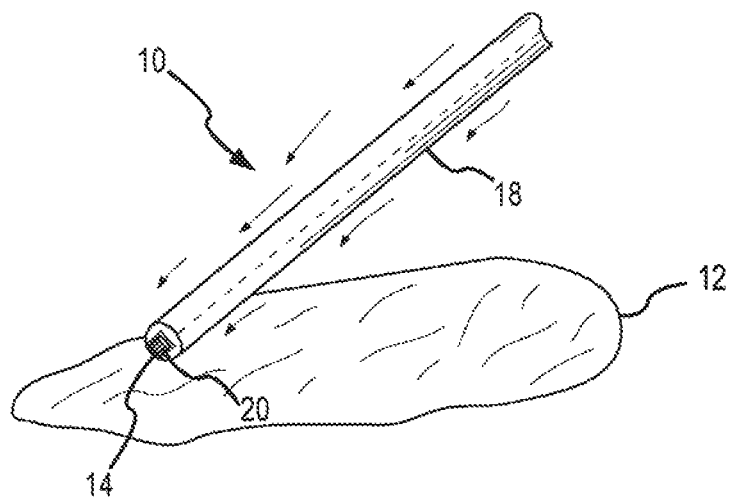
FIGS. 1a and 1b are fragmentary isometric views depicting exemplary contact between a catheter and adjacent target tissue (e.g., moving myocardium).

Exemplary embodiments of a tissue assessment system and methods of use to assess tissue and/or contact between a catheter and tissue, along with methods for creating ablative lesions (possibly while actively protecting untargeted tissue), are described herein with components for the system depicted in the figures. Exemplary systems comprise a catheter which can be inserted into the patient, e.g., an ablation catheter for forming ablative lesions inside, on or about the patient's heart. During an exemplary ablation procedure, a user (e.g., the patient's physician or a technician) may insert the catheter into one of the patient's blood vessels, e.g., through the femoral vein in a leg or via a branch of the subclavian vein near the patient's neck. The user, guided by a machine vision system or localization system (e.g., an impedance-based or magnetic-based imaging device, or a fluoroscopy or magnetic resonance imaging device) moves the catheter into contact with a portion of the patient's heart or vascular tissue.

When the catheter reaches a desired location (e.g., adjacent to tissue comprising part of a patient's myocardium), acoustic transducers at the distal portion of the catheter can be activated to electrically map the tissue around the catheter and locate target tissue. After locating the target tissue, the user must move the catheter into contact with the target tissue before assessing the tissue and/or applying ablative energy to form an ablative lesion or lesions. In exemplary embodiments, the ablative energy can be in the form of acoustic or ultrasonic energy. In other embodiments, the ablative energy can be generated by conventional radiofrequency electrodes or other suitable means. Understanding the tissue properties (e.g., number and type(s) of tissue layers, tissue depth, and other characteristics of the tissue) and determining the appropriate level of contact is often critical to form quality ablative lesions on the target tissue, at the desired depth, and without damaging surrounding tissue in the heart or other tissues or anatomical structures elsewhere in the patient's body.

As described further below, the catheter may comprise one or more acoustic transducers which generate electric signals in response to the catheter coming into proximity or contact with a surface (e.g., target tissue within the heart). When the catheter is placed close to a tissue boundary, such as a blood vessel, endocardial wall, or epicardial surface, the acoustic transducers emit acoustic energy which passes at least partly through the media, such as blood, and is reflected from the tissue boundary back to the transducers. The transducers detect changes in the acoustic signal (between the emitted and received signals). For example, changes can be detected in the transit time, frequency, wavelength, velocity, pressure, and/or intensity, to name only a few examples of acoustic properties which can be quantized. These changes can be used to provide feedback that is indicative of tissue parameters and tissue contact (e.g., the proximity of the electrode in the catheter relative to the tissue, contact of the electrode with the tissue, thickness of the tissue, and/or other properties of the tissue).

In an exemplary embodiment, the physiological properties of the tissue can be monitored before, during, and/or after a diagnostic or therapeutic procedure (e.g., an ablation or other procedure) to sense tissue modification (e.g., either reversible or irreversible) such as lesion formation. In other exemplary embodiments, the transducers themselves and/or separate shielding devices can be utilized to cause wave cancellation at specific tissue boundaries, thereby providing additional protection to surrounding tissue and/or anatomical structures.

Accordingly, embodiments of the present invention provide a number of advantages, including, for example, the ability to apply a reasonable, safe, and effective amount of ablative energy to a target tissue while mitigating tissue contact problems given the results of the assessment or quanitization of the tissue with the acoustic or ultrasonic transducer. The invention also facilitates enhanced tissue contact in difficult environments (e.g., during lesion formation on a moving surface inside a beating heart, and adjacent other sensitive tissues or anatomical structures).

Figure 1B:
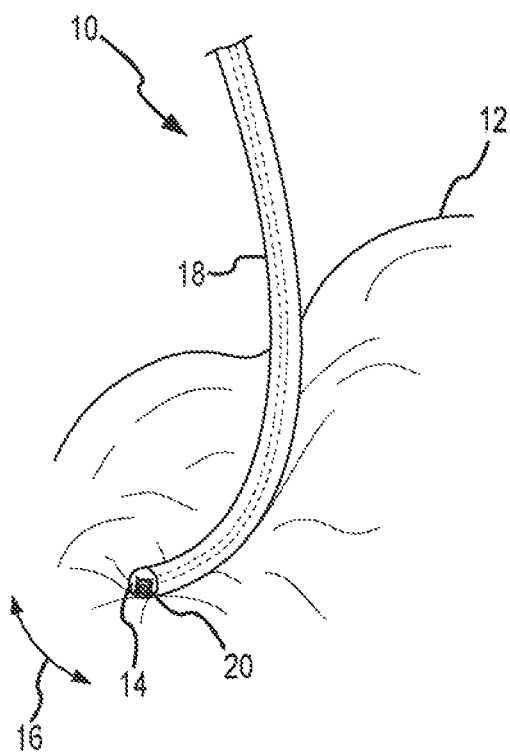

FIGS. 1a and 1b illustrate exemplary contact between a catheter 10 and target tissue 12 (e.g., moving myocardium in the heart). In FIG. 1a, the catheter 10 is shown having little, if any, contact with the target tissue 12, e.g., as the distal end portion 14 of catheter 10 can be "floating" adjacent to the target tissue 12 as the user is positioning the catheter 10 in the heart for an ablation procedure. In FIG. 1b, the catheter 10 is shown in contact with the target tissue 12.

When the catheter 10 is in sufficient or "good" contact with the target tissue 12, given the results of the acoustic assessment(s) of the tissue, the catheter 10 may move or be deflected by movement of the target tissue 12 generally in the directions illustrated by arrows 16. Acoustic transducer 20, which may comprise a plurality of individual transducers, in the catheter 10 can be used to assess position and/or movement of the catheter 10 in near real-time, assess contact between the catheter 10 and the target tissue 12, map the target tissue 12, assess the tissue itself (e.g., tissue structure including the number of tissue layers and interfaces), assess lesion formation, and/or apply ablative energy, as described more fully below, so that higher quality lesions can more accurately and effectively be established (e.g., continuous, transmural, of sufficient depth or volume).

Before continuing, it is noted that the contact and motion illustrated by FIG. 1b is shown for purposes of illustration and is not intended to be limiting. Other contact and motion may also exist and/or be desired by the user. The definition of sufficient or "good" contact may depend at least to some extent on various operating conditions, such as, e.g., the type of target tissue, desired depth of the ablation lesion, and power and duration of the applied ablative energy, to name only a few examples.

It is also noted that other components typical of systems which are conventionally implemented for tissue ablation or for other therapeutic procedures implemented via catheters (e.g., delivery of a drug or therapeutic agent) are not shown or described herein for purposes of brevity. Such components may nevertheless also be provided as part of, or for use with, the catheter 10. For example, these systems commonly include or are used in conjunction with an ECG recording system, and/or various controls for performing an ablation procedure. Such components are well understood in the medical device arts and, therefore, further explanation is not necessary for a complete understanding of the invention.

As mentioned above, the catheter 10 may comprise one or more acoustic transducers 20. Exemplary acoustic transducers may implement magnetic, piezoelectric (e.g., ceramic or polymer-based), micro-electro mechanical systems (MEMS), capacitive MEMS ultrasound transducers (cMUT), electrostatic, or any other suitable acoustic energy generating and/or receiving means that are now known or later developed. Acoustic transducers 20 emit or transmit or otherwise propagate acoustic energy (e.g., sound waves such as ultrasound waves). The acoustic transducer 20 may emit the acoustic energy according to any of a wide variety of mechanisms, e.g., as pulses or as a constant output. The emitted acoustic energy at least in part penetrates the surrounding media (e.g., blood or other fluids) and tissues. The acoustic energy is reflected at least in part by the surrounding environment. The reflected acoustic energy is returned to and received by the acoustic transducers 20 and can be used to generate electrical signals representative of the environment.

It is noted that the acoustic transducer 20 may emit and receive acoustic energy simultaneously, or transmission/reception can be interleaved over time (e.g., alternating output and response functions). In addition, output of the acoustic energy can be modulated, gated (e.g., turned off and on), or otherwise modified (e.g., over time from high to low frequency) to control delivery and achieve a predictable response.

The resulting electrical signals can be processed and/or otherwise output for the user, as explained in more detail below (e.g., by measuring velocity of the acoustic waves in the tissue or surrounding media). The output may aid the user to determine when the catheter 10 is positioned with the desired level of contact (e.g., with respect to a moving target tissue 12), to map the target tissue 12 and surrounding environment, to assess the tissue (e.g., provide depth information within a tissue, tissue thickness, or distance to an anatomical feature, assess lesion formation, and/or apply ablative energy to create a lesion. For example, feedback can be provided to the user to provide a warning or other indication during treatment of the tissue.

Figure 2A:
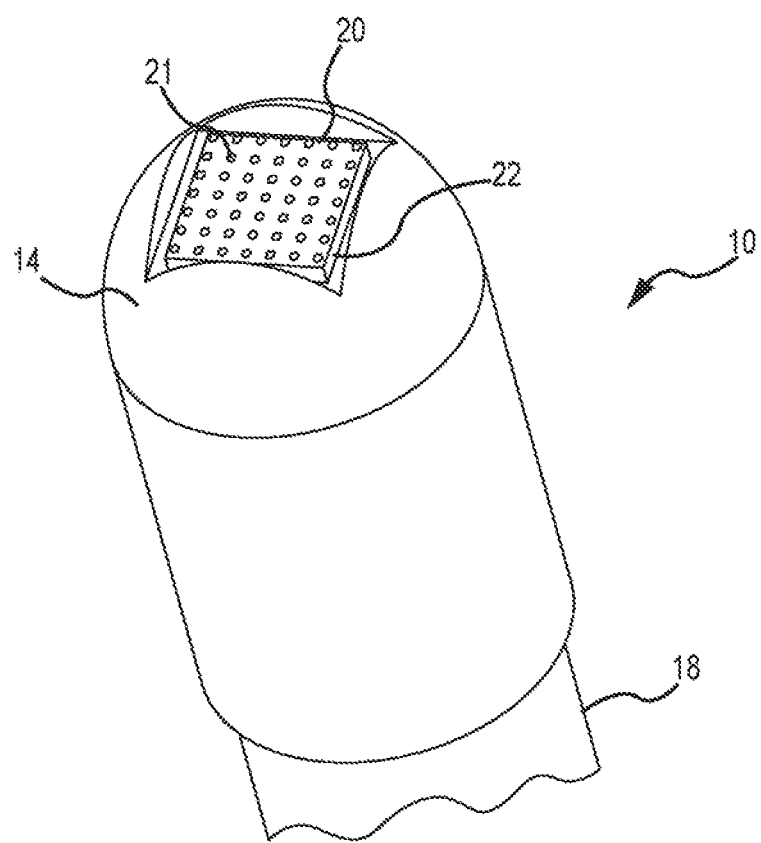
FIG. 2a is an isometric view of a portion of an exemplary catheter with an acoustic transducer located at the catheter's tip.
Figure 2B:
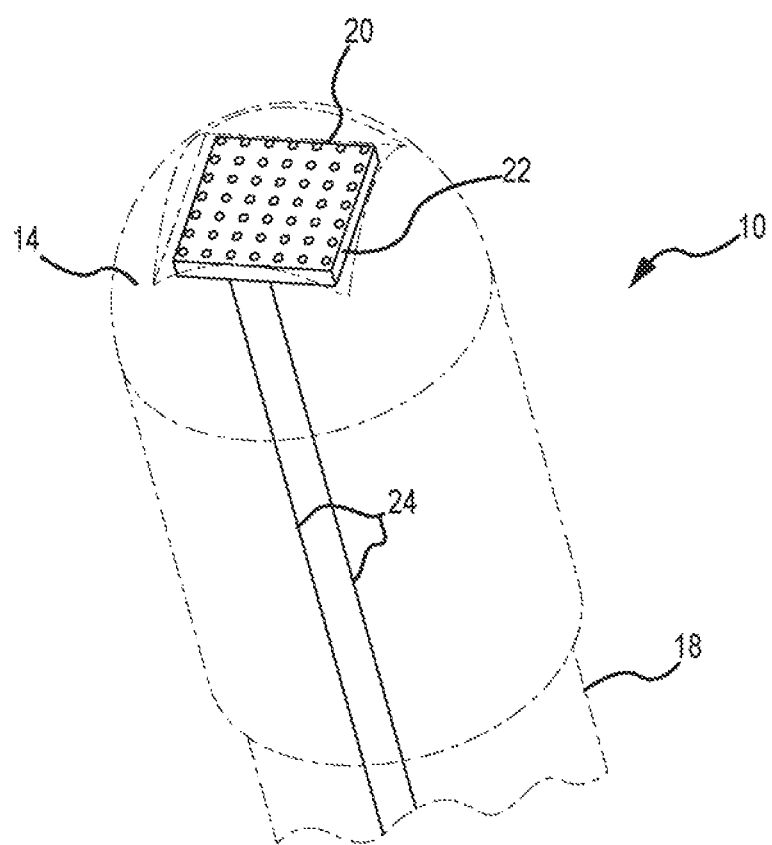
FIG. 2b is a view of the portion of catheter with portions depicted in phantom as was shown in FIG. 2a, showing the acoustic transducer in more detail.

FIG. 2a is an isometric view of a portion of an exemplary catheter 10 with an acoustic transducer 20. FIG. 2b is a "transparent" or "see through" view of the portion of catheter 10 shown in FIG. 2a, showing the acoustic transducer 20 in more detail. The portion of catheter 10 shown in FIGS. 2a and 2b is the portion which can be inserted into the patient's heart for an assessment and/or ablation procedure (e.g., the portion of catheter 10 shown in FIGS. 1a and 1b).

Catheter 10 may comprise a flexible catheter shaft 18 (also visible in FIGS. 1a and 1b). The flexible catheter shaft 18 can be made of a plastic or other suitable material that enables the catheter 10 to be readily inserted into the patient's heart through the blood vessels, and to be moved or deflected by movement of an adjacent tissue (e.g., target tissue 12 shown in FIGS. 1a and 1b).

An acoustic transducer 20 can be provided at a distal portion 14 of the catheter shaft 18. The acoustic transducer 20 may include one or more (a plurality) of transducer elements (one of the elements is labeled 21 in FIG. 2a and FIG. 2b). Generally, a transducer element converts one type of energy to another. For example, an acoustic transducer element can be configured to convert a vibrational energy into acoustic waves; and/or the acoustic transducer element may convert acoustic waves into a vibrational energy. The energy can be translated to/from electrical signals. For example, an electrical signal provided at the catheter 10 can be used to generate a vibrational energy which is emitted by the transducer 20 as acoustic waves. The acoustic waves can be reflected from the surrounding environment. The acoustic waves can be used to increase the temperature of the tissue 12, e.g., for creating lesions. The acoustic waves reflected from the surrounding environment (e.g., from the adjacent tissue 12) can be received at the transducer and detected as vibrational energy, which may then be translated into electrical signals corresponding to the received acoustic waves. These electrical signals can be processed and/or otherwise output for a user to employ for assessment procedures.

There are various types of transducer elements, including emitters, receivers, and combination emitter/receivers. An emitter (or actuator) generates and outputs acoustic energy by converting an electrical signal into nonelectrical acoustic energy. A receiver (or sensor) receives acoustic energy (e.g., by detecting vibrations) and converts the acoustic energy to electrical signals. The combination emitter/receivers can be switched back and forth (e.g., on the order of many times each second) between emitting acoustic waves and detecting acoustic waves.

It is noted that the acoustic transducer 20 can be implemented with transducer elements 21 comprising any of an emitter, receiver, combination emitter/receiver, or a combination of these (e.g., separate emitters and receivers, and combination emitter/receivers). It is also noted that the acoustic transducer 20 may include one or more transducer elements 21 arranged in any suitable manner. The transducer elements 21 can be actuated selectively, concurrently, or sequentially, depending on the desired result and to avoid undue heating of the elements, for example.

Figure 2C:
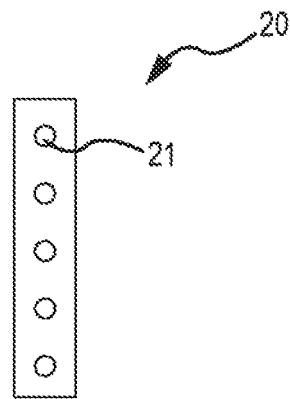
FIGS. 2c-2h show alternative exemplary configurations of the acoustic transducer.
Figure 2D:
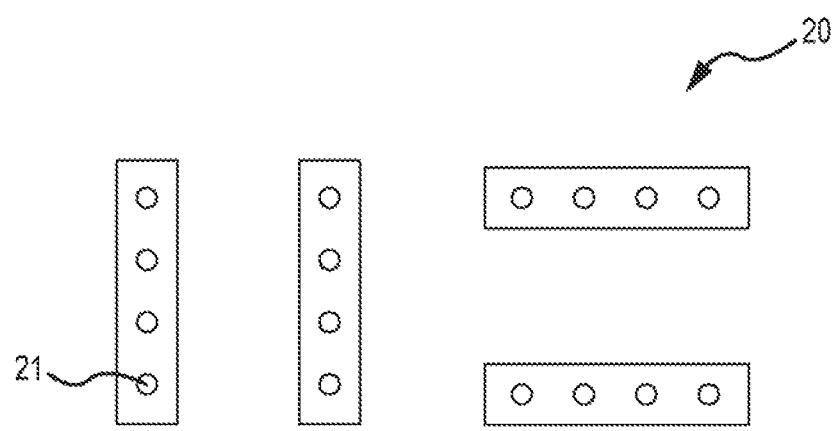
Figure 2E:
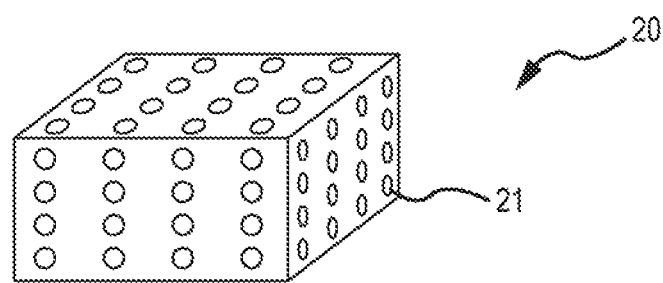
Figure 2F:
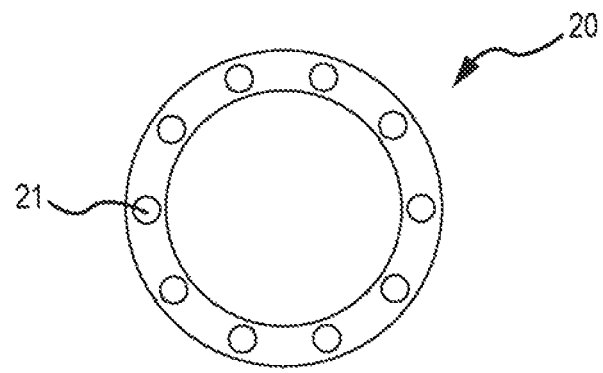
Figure 2G:
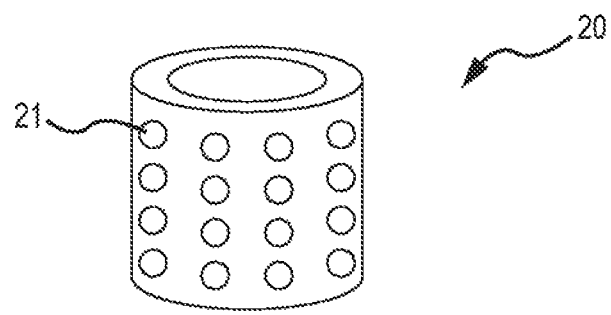
Figure 2H:
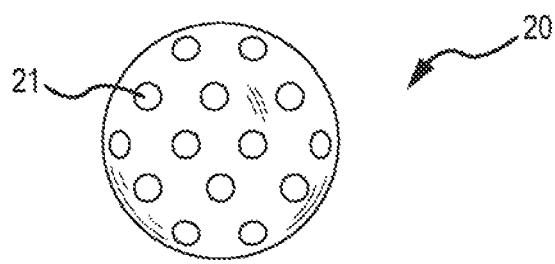

In FIGS. 2a and 2b, a plurality of transducer elements 21 are arranged in a two-dimensional array. However, the arrangement of transducer elements 21 is not limited to a two-dimensional array. For example, the transducer elements 21 can be arranged as a one-dimensional array (FIG. 2c), as multiple one-dimensional arrays (FIG. 2d), a three-dimensional array (FIG. 2e), a circular or other geometric arrangement (circular is shown in FIG. 2f), cylindrical arrangement (FIG. 2g), spherical arrangement (FIG. 2h), and so forth. Multiple transducers 20 may also be implemented, e.g., to cross-check signal processing capabilities and signal integrity, and/or to determine positions (e.g., in the X, Y, and Z directions), and/or to determine temporal information (e.g., position with respect to time).

It is also noted that the transducer 20 can be operated in a uni-polar mode (i.e., a single transducer element 21 being activated at any given time) or multi-polar mode (e.g., dipolar, quadrapolar, etc.). The specific operational configuration can depend on the desired use. For example, the transducer 20 can be implemented in a multi-polar mode to effect phase shift/lag to nullify a signal at a predetermined distance from the transducer 20 (e.g., to protect other tissues or anatomical structures), or to shape the field of use (e.g., for targeting specific tissue and/or specific layers of the tissue).

With reference again to FIGS. 2a and 2b, acoustic transducer 20 is shown housed within the catheter shaft 18. For example, acoustic transducer 20 can be provided within an insulated cavity or a compliant section formed within the catheter shaft 18. In addition to housing the acoustic transducer 20 in the catheter 10, and protecting the acoustic transducer 20 from external damage or corrosion, the compliant section may also serve as a low pass filter. That is, the compliant section attenuates high frequency "noise" signals caused, e.g., by minor vibrations from intermittent contact during positioning of the catheter 10 adjacent the target tissue. Accordingly, high frequency noise signals are damped, or even non-existent, as output for the user.

The acoustic transducer 20 can be positioned behind an acoustic lens or window 22. Window 22 can be any suitable material that mechanically focuses the acoustic energy to the desired output area. The window 22 offers protection for the acoustic transducer 20. Accordingly, the window 22 does not necessarily need to be transparent. Semi-transparent or even opaque windows can be utilized so long as the acoustic signals may pass through the window 22. In order to focus the acoustic energy to the desired output area, the window 22 can be configured in such a manner so as to affect direction of the acoustic signals being emitted. For example, the window 22 can be provided so that the acoustic signals are only emitted/received through predetermined locations of the distal end portion 14 of the catheter 10. Other blocking material (not shown) may also be utilized for directional configuration of the acoustic signals. Although not shown, an acoustic filter may also be provided within the window 22 to filter undesired return signals (or noise).

The acoustic transducer 20 can be electrically connected via suitable wiring 24 through the catheter shaft 18 to a generator (not shown), such as, e.g., an acoustical energy generator. The transducer 20 is thus operable to emit acoustic energy near the tip portion 14 of the catheter 10 for mapping and/or for forming ablation lesions on the target tissue during ablation procedures. Electrical wiring may also be connected to the acoustic transducer 20 and extend through the catheter shaft 18 to deliver electrical signals from the acoustic transducer 20 to a data acquisition/processing/output device (not shown), such as, e.g., an echocardiogram device or a recording device or a display. Alternatively, a wireless connection can be implemented, e.g., by providing a transmitter in the catheter and a receiver in association with the data acquisition/processing/output device.

In an exemplary embodiment, the acoustic transducer 20 may include laminated transducer elements 21, having a plurality of laminated layers. Laminating a transducer element 21 increases its sensitivity. The laminated layers may include a protective coating. Protective coating can be any suitable material, e.g., Mylar®. However, it is noted that the laminated layers are not limited to any particular material and/or configuration.

In addition, the acoustic transducer 20 may also be housed in a compliant section of the catheter. The compliant section acts as a low pass mechanical filter for the sensor and attenuates the high frequency noise signal when the catheter moves in response to movement of the myocardial wall during intermittent contact.

It is noted that the acoustic transducer 20 is not limited to being centrally oriented in the catheter shaft 18. Acoustic transducer 20 can be offset from the central axis. Also by way of example, the acoustic transducer 20 is not limited to being housed within the catheter shaft 18. Acoustic transducer 20 can be laminated to an outer surface of the catheter shaft 18.

The acoustic transducer 20 can be oriented within the catheter shaft 18 to affect directional configuration and/or delivery of the acoustic signals and/or to provide the desired level of sensitivity. By way of example, acoustic transducer 20 is shown in FIGS. 2a and 2b centrally oriented in the catheter shaft 18, with the acoustic elements 21 arranged substantially parallel to the central axis of the catheter shaft 18.

Of course the acoustic transducer 20 described above with reference to FIGS. 2a and 2b is for purposes of illustration and not intended to be limiting. Other acoustic transducers may also be implemented. Nor are acoustic transducers limited to use with any particular type or size of acoustic material. Selection, number, and positioning of the acoustic transducer 20 for use with the catheter 10 can be application-specific and depend at least in part on one or more design considerations, such as, but not limited to, the desired sensitivity and/or spatial constraints for housing the acoustic transducer.

Figure 3A:
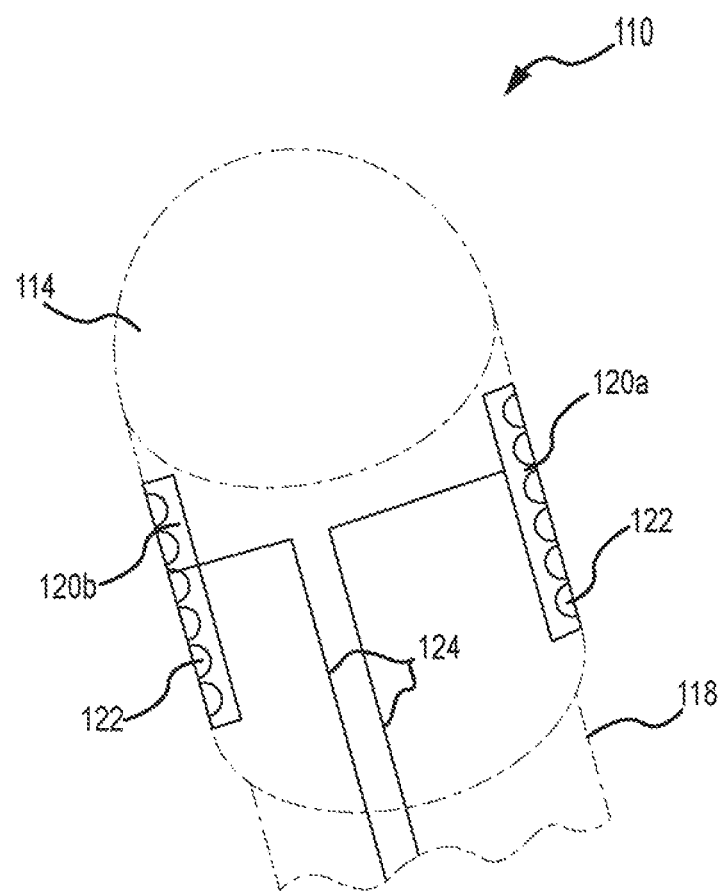
FIG. 3a shows another embodiment of a catheter.

FIG. 3a shows another embodiment of a catheter 110. It is noted that 100-series reference numbers are used in FIG. 3a to refer to like elements described above. Therefore, the description of some elements may not be repeated in the discussion of FIG. 3a.

In this embodiment, catheter 110 may comprise a flexible catheter shaft 118 with a plurality of acoustic transducers 120a and 120b (although only one transducer may also be used). The acoustic transducers 120a and 120b are oriented such they are substantially parallel to the central axis of the catheter shaft 118. In this example, however, the acoustic transducers 120a and 120b are positioned off-center, or eccentrically away from the central axis of the catheter shaft 118. Although only two acoustic transducers 120a and 120b are shown FIG. 3a, it is noted that any number of acoustic transducers can be provided and spaced about the distal end portion 114 of the catheter 110 in any suitable manner (e.g., spaced equidistantly about the perimeter).

Such a configuration can be implemented with irrigated catheters. Irrigated catheters typically include one or more fluid tubes (not shown) for delivering cooling fluids (e.g., saline), medication, or other fluids to the tissue. These fluid tubes may extend through the catheter 110 along or in the general direction of its central axis, e.g., to protect the fluid tubes from damage and the potentially harmful release of the fluid elsewhere in the patient's body. Therefore, positioning the acoustic transducers in the catheter shaft 118 substantially as shown in FIG. 3a enables the use of acoustic transducers with conventional irrigated catheters.

Such an embodiment may also be implemented to provide greater response sensitivity. That is, positioning the acoustic transducers off-center and closer to the outer diameter of the catheter 110 enables the acoustic transducers to receive stronger (higher amplitude) reflected signals.

Figure 3B:
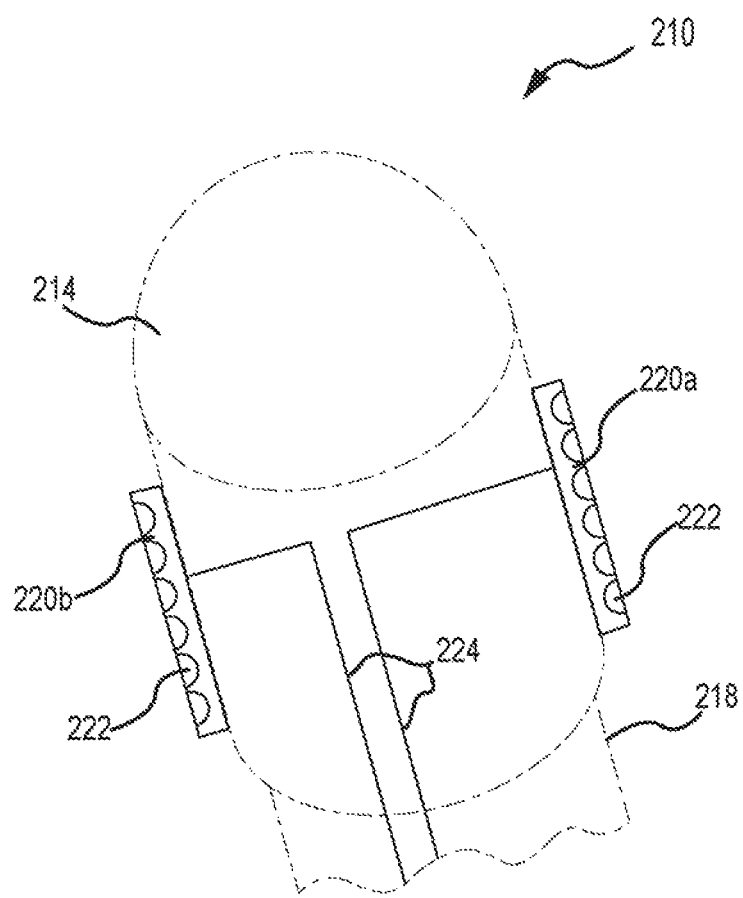
FIG. 3b shows another embodiment of a catheter.

FIG. 3b shows another embodiment of a catheter 210. It is noted that 200-series reference numbers are used in FIG. 3b to refer to like elements described above. Therefore the description of some elements may not be repeated in the discussion of FIG. 3b.

The catheter 210 may comprise a flexible catheter shaft 218 with a plurality of acoustic transducers 220a and 220b. While two acoustic transducers 220a and 220b are shown in FIG. 3b, any number (one or more) of acoustic transducers can be provided in any suitable arrangement in the catheter tip 214 or along the length of the catheter 218. In FIG. 3b, the acoustic transducers 220a and 220b are oriented such that each is substantially parallel to the central axis of the catheter shaft 218. In this example, however, the acoustic transducers 220a and 220b are provided on the outer surface of the catheter shaft 218. For example, each of the acoustic transducers 220a and 220b can be applied to the surface of the catheter shaft 218 and insulated by a compliant layer.

In an exemplary embodiment, acoustic transducers 220a and 220b can be positioned on diametrically opposite surfaces of catheter shaft 218. The embodiment shown in FIG. 3a can be implemented for assessing contact with a moving tissue in endoluminal flow applications, e.g., when the catheter 210 is surrounded by blood flowing through the heart while positioning the catheter 210 against the heart wall. Output from the acoustic transducers 220a and 220b indicate if the catheter 210 is free-floating in a hydrodynamic environment (e.g., surrounded by blood flow as shown in FIG. 1a), or if the catheter 210 is positioned in contact with the moving tissue (e.g., as shown in FIG. 1b).

Hydrodynamic pressure fluctuations are isotropic in nature. When the catheter 210 is being positioned within the patient's heart, the blood flow through the heart around the catheter 210 exerts approximately the same pressure on the catheter 210 in all directions. Accordingly, the acoustic signals are approximately uniform or the same for each of the acoustic transducers 216a and 216b (i.e., the waveforms are "in-phase" with one another). Such output indicates that the catheter 210 is free-floating and not in contact with the moving tissue.

When the catheter 210 is free-floating, the acoustic signals being received by each transducer 220a and 220b are almost the same, and the respective waveforms are approximately in-phase with one another. Under ideal conditions, these waveforms can be combined to have a canceling or additive effect. Of course a patient's heart may not provide such ideal conditions. However, the waveforms should approximately cancel one another, thereby indicating that the catheter 210 is in an endoluminal flow environment.

When the catheter 210 is in contact with the moving tissue, one of the acoustic transducers (e.g., 220a) receives a return signal much faster than the other acoustic transducer (e.g., 220b). Accordingly, the output from the acoustic transducers 220a and 220b is "out-of-phase" with one another. Such output indicates that the catheter 210 is in contact with the tissue. Other methods for determining contact may also be implemented, such as, e.g., comparing the received waveform with a waveform generated for the patient's heartbeat.

Figure 4A:
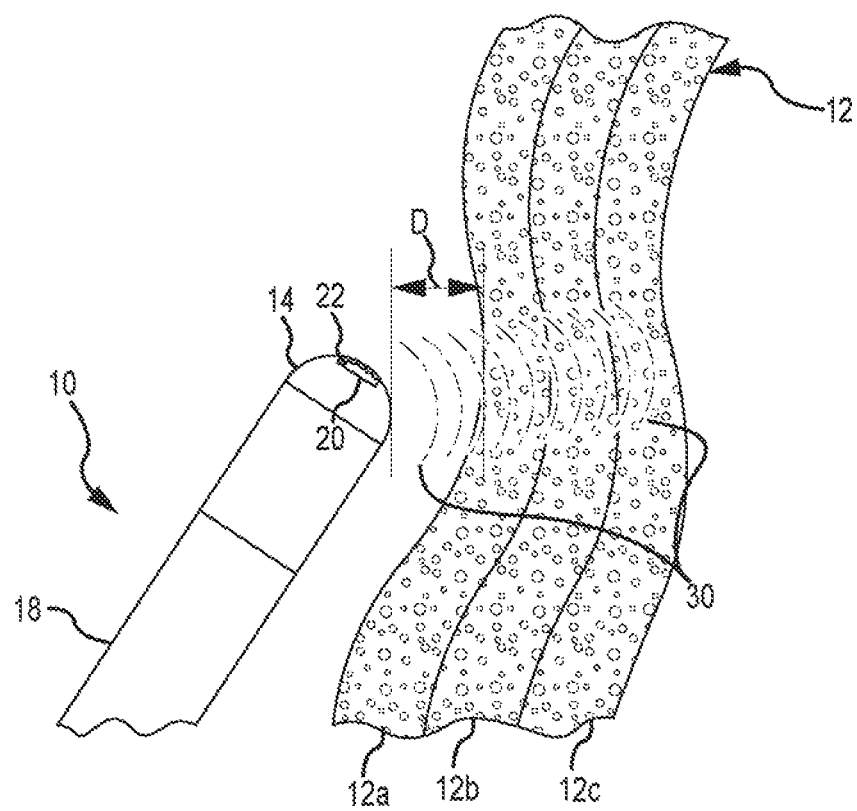
FIGS. 4a and 4b illustrate exemplary operation of an acoustic transducer as the transducer can be utilized to assess tissue contact and/or to emit ablative energy.
Figure 4B:
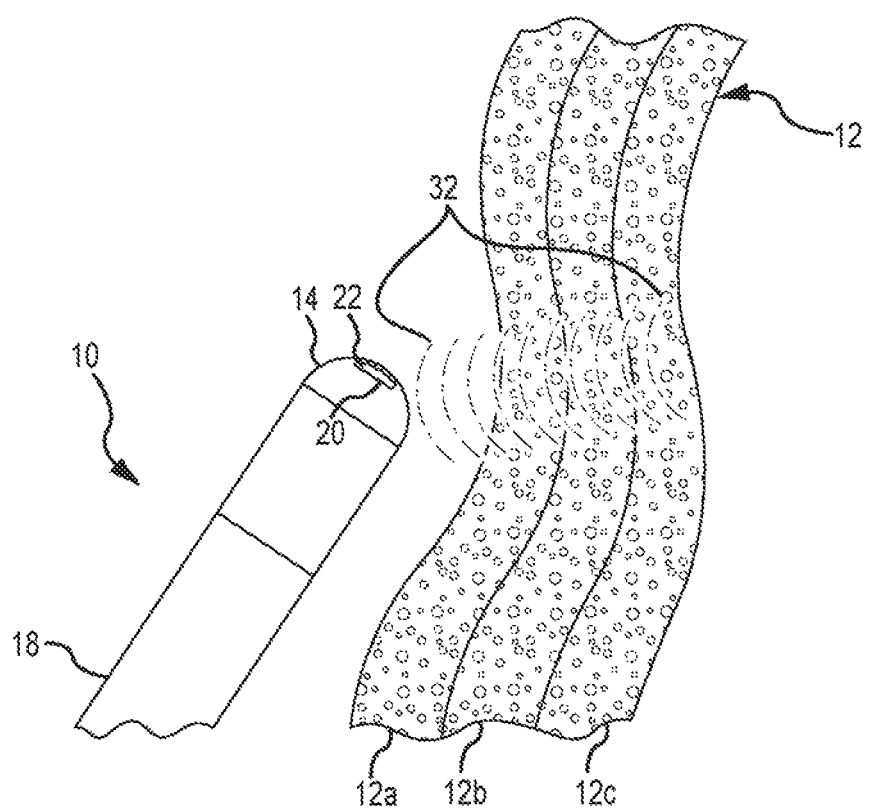

FIGS. 4a and 4b illustrate exemplary operation of an acoustic transducer 20 as the transducer can be utilized to assess tissue contact and/or to emit ablative energy. During use, an acoustic pulse (e.g., a "ping") (illustrated in FIG. 4a by acoustic "waves" 30) is generated and emitted in a particular direction. In FIG. 4a, the acoustic pulse 30 is shown being emitted toward the tissue 12. Part or all of the acoustic pulse 30 is reflected back from the tissue 12 (e.g., as an echo) (illustrated in FIG. 4b by acoustic waves 32) to the transducer 20. The reflected pulse or echo 32 is detected by the transducer 20 (e.g., through the receiver path). By measuring the difference in time between the pulse 30 being transmitted and the echo 32 being received, it is possible to determine the distance D from the transducer 20 (or the catheter 10) to the tissue.

Determining the distance D (or "ranging") can be performed by multiplying half the time from the signal's outgoing pulse to its return by the speed of sound in the medium (e.g., blood or tissue). In one embodiment, the transit time (t) between the emitted and reflected acoustic signals can be used to measure the distance ($d_e$) between the catheter tip (e.g., where an ablation electrode resides) and the tissue boundary according to the following formula:

$$d_e = c_m \times \frac{t}{2}$$

where $c_m$ is the velocity of sound in the medium.

As the transit time t approaches 0, the output is indicative of the electrode coming into complete contact with the tissue (i.e., $d_e$ approaches 0).

In another embodiment, the thickness of the tissue ($d_t$) can be measured from, for example, the transit time (t) of the reflected wave within the tissue. For example, when the electrode is in contact with the tissue, the acoustic energy emitted from the transducer travels through the thickness of the tissue and is reflected from the opposite surface of the tissue back to the transducer. The thickness $d_t$ of the tissue is then obtained from the following formula:

$$d_t = c_t \times \frac{t}{2}$$

where $c_t$ is the velocity of sound in the tissue.

In another embodiment, the time from emitting an acoustic pulse to receiving the echo is measured and converted based on the speed of sound. The measurement can be made by one or more transceiver element, and analyzing the arrival time relative to each (or by measuring the relative amplitude or other characteristic of the signals). A plurality of transceiver elements can be used to reduce the spatial response. The received signal may then be passed through various forms of signal processing. Further processes can be carried out to characterize and localize the tissue.

It is noted that the speed of sound should be adjusted based on the medium where the transducer is being implemented. Of course, the measured travel time of acoustic pulses is dependent on a variety of other factors as well. For example, the measured travel time can be dependent on the type of acoustic pulse being utilized (e.g., ultrasound or high-frequency ultrasound). Other exemplary factors include, but are not limited to, the type of tissue (e.g., fatty tissue versus muscular tissues versus scarred tissue), tissue versus blood, temperature, salinity, and pH.

The acoustic energy can be emitted at a constant frequency or at changing frequencies (to allow pulse compression). Pulse compression can be achieved using digital correlation techniques. A filter may also be utilized that is wide enough to cover Doppler changes due to movement of the target tissue. When single frequency transmissions are used, the Doppler Effect can be used to measure movement of the tissue. The difference in frequency between the transmitted and received signal is measured and converted into a velocity signal. Since Doppler shifts can be introduced by either movement of the catheter 10 (e.g., transducer 20) and/or movement of the tissue 12, Doppler shifts may need to be corrected for movement of the catheter 10.

FIG. 4a and FIG. 4b also illustrates exemplary operation of an acoustic transducer 20 in different layers 12a-c of the tissue 12 and for different assessments (e.g., assessing contact, assessing lesion formation, and resulting lesions). The acoustic coupling can be quantized and correlated with, among other factors, the acoustic impedance of the tissue, the amount of energy in the tissue, the temperature of the tissue (e.g., whether the temperature is raised sufficiently to create a good lesion), etc.

By way of example, different acoustic properties can be observed for layered tissue (e.g., heart tissue) versus non-layered tissue. Layered tissue 12a-c may comprise different types of cells (e.g., bundles of muscle and/or fatty cells), each having discrete interfaces (e.g., fluid interfaces); or the same type of cells juxtaposed between discrete interfaces. These characteristics can be used in conjunction with the acoustic coupling methods described herein to assess tissue contact and/or lesion formation at the different tissue layers. Indeed, these different layers, and interfaces between the layers can be clearly detected by the acoustic pulses, helping to map the tissue.

In addition, pre-ablative tissue exhibits different characteristics (e.g., reflects acoustic waves differently) than tissue which has been ablated; and different levels of ablation exhibit different characteristics. For example, the amplitude of the reflected acoustic signals increases the more a tissue is ablated. These characteristics may also be used to assess lesion formation.

Edema (i.e., the swelling from excessive accumulation of fluid in tissue), which occurs in tissue in response to the tissue being ablated, can also be quantified using the acoustic methods described herein. For example, the velocity of the acoustic waves increases in response to thickening edema. Accordingly, quantifying the degree of edema at a lesion site may also be used to assess the state of a lesion in real-time during formation of the lesion.

While the acoustic methods for quantizing the acoustic response of various tissue properties for mapping tissues and/or assessing lesion formation can be implemented with conventional ablative elements (e.g., RF electrodes, laser, microwave, etc.), acoustic energy may also be utilized to create lesions in desired spots/areas of target tissue and/or at desired tissue depths or tissue interfaces. A therapeutic acoustic energy referred to as HIFU (High Intensity Focused Ultrasound) can be employed, either using the same or separately provided acoustic transducers 20. As the name implies, HIFU uses high intensity focused ultrasound emitters to raise the temperature of the tissue.

Therapeutic ultrasound is a minimally invasive, even considered non-invasive, technique for delivering acoustic energy to tissue. HIFU works to create lesions as follows. As acoustic waves propagate through the tissue, part of the acoustic energy is absorbed and converted to heat. When the temperature of the tissue rises sufficiently (e.g., between about 60° C. to 90° C.), the tissue necroses via thermal ablation. Microbubbles form at sufficiently high intensities and cause cavitation. During cavitation, high temperatures cause the microbubbles to collapse, thus forming the lesion in the tissue.

Although a specific example is given herein with respect to HIFU acoustic energy, it is noted that the invention is not limited to use with any particular type of acoustic energy. The type of acoustic energy employed will depend on a wide variety of factors, including, but not limited to, the desired treatment, the type of tissue being treated, and the desire to avoid adverse side-effects. Other applications of acoustic energy may also include ablation for tumor reduction, hyperthermia treatments (low-level heating of the tissue), and for activating or enhancing delivery of drugs.

Using the techniques described herein for detecting tissue contact, tissue depth, and the canceling effect (described below), the acoustic signals can be further focused in a desired target area and/or target depth to control lesion formation only at the desired target area without damaging surrounding tissue or anatomical structure. Exemplary methods for controlling lesion formation only at the target area may include, but are not limited to, controlling phase, amplitude, frequency, and/or timing of the acoustic signal. In addition, the signal can be alternated or interleaved with a low energy signal. A cooling fluid (e.g., saline or pericardial fluid) may also be delivered to the tissue simultaneously or interspersed with the acoustic signal to control tissue temperature and/or to enhance acoustic coupling between the acoustic transducer 20 and the tissue.

It is noted that the various techniques for mapping tissue, assessing lesion formation, and creating lesions can be implemented by the same catheter or with different catheters. Likewise, the same transducers can be utilized for more than one purpose; or single-purpose transducers can be provided within the catheter. The transducers can be operated simultaneously or alternatingly (e.g., sequentially) to carry out the desired operations.

During operation, acoustic transducer 20 generates electrical (voltage) signals indicative of the acoustic coupling with the tissue (e.g., for mapping and to control lesion formation). These electrical signals can be output for viewing by the user, e.g., as output on a display device.

FIGS. 5*a*-5*d* show exemplary output waveforms 50-53 corresponding to electrical signals generated by an acoustic transducer 20 in a catheter 10 inserted into the patient's heart in response to sending (solid lines) and receiving (dashed lines) acoustic signals. These waveforms can be displayed, e.g., on an EKG display device, or simply utilized internally by a processor.

Figure 5A:
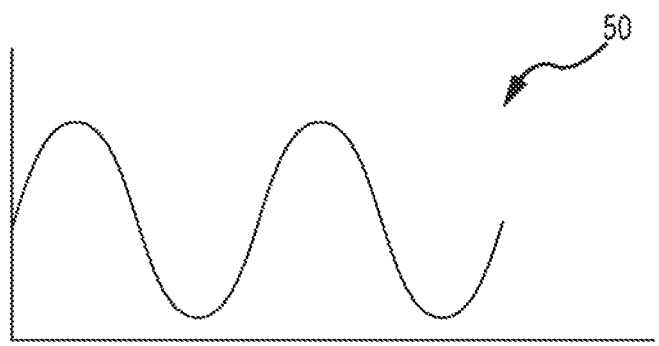
FIGS. 5a-5d show exemplary output waveforms corresponding to electrical signals generated by an acoustic transducer in a catheter inserted into the patient's heart in response to sending (solid lines) and receiving (dashed lines) acoustic signals.
Figure 5B:
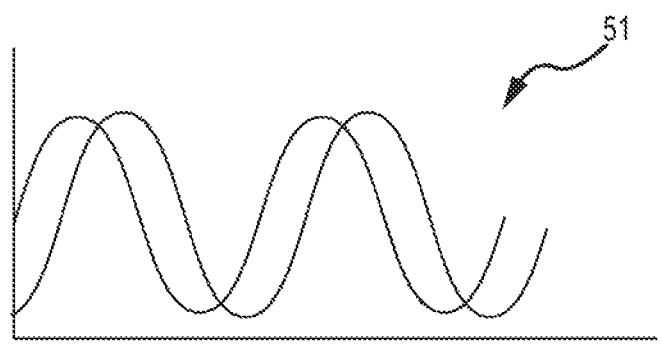

FIG. 5*a* and FIG. 5*b* show output acoustic signals. FIG. 5*a* shows a waveform 51 of an emitted acoustic pulse (or "ping") as it can be displayed as an electrical signal (e.g., the electrical signal used to generate the output acoustic signal). FIG. 5*b* shows how the periodicity of the emitted acoustic pulse can be varied. For example, the periodicity can be varied for different types of medium (e.g., different types of tissue, or where more blood is present). Different periodicity may also be useful in detecting multi-layered tissues (e.g., as shown in FIGS. 4*a* and 4*b*).

Figure 5C:
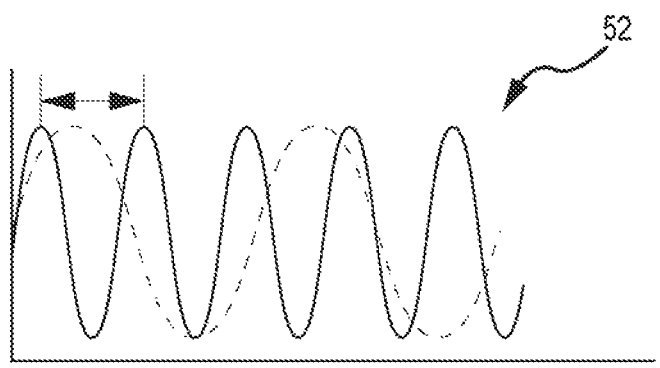
Figure 5D:
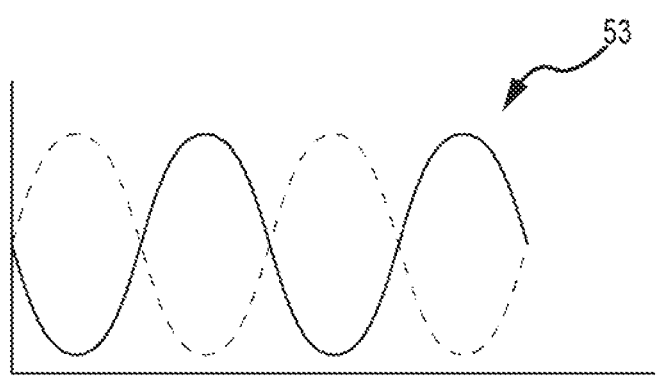

FIG. 5*c* and FIG. 5*d* show output acoustic signals and the corresponding reflected acoustic signals. FIG. 5*c* shows a waveform 52 wherein the return signal (or "echo") is offset from the emitted pulse (or "ping"). The waveforms can be compared, e.g., using the formulas discussed above, to determine the distance D (FIG. 4*a*) from the transducer 20 to the tissue 12 and used to assess catheter 10 contact with the tissue 12. The waveforms may also be evaluated to assess lesion formation.

Figure 7:
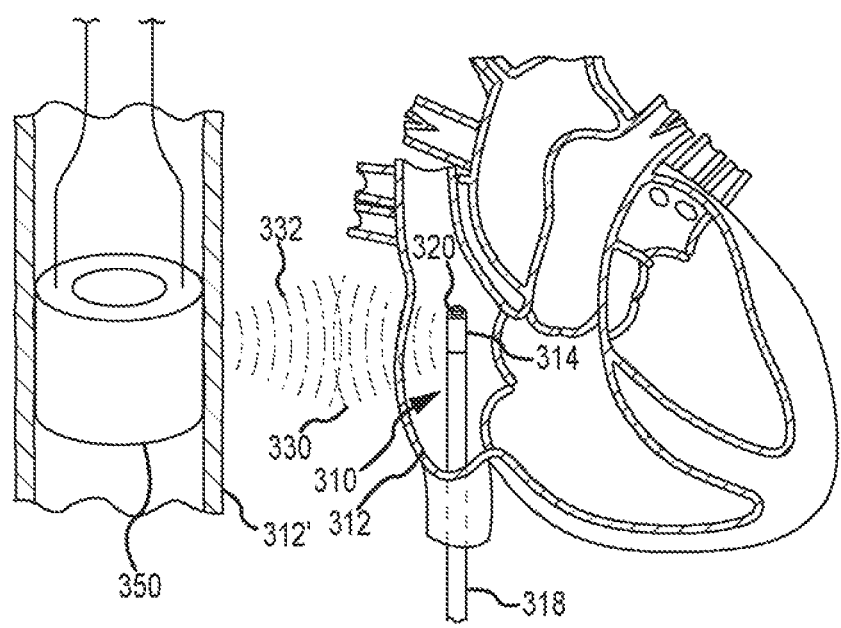
FIG. 7 is a cross-sectional view of a portion of another exemplary catheter with an acoustic transducer.
Figure 8:
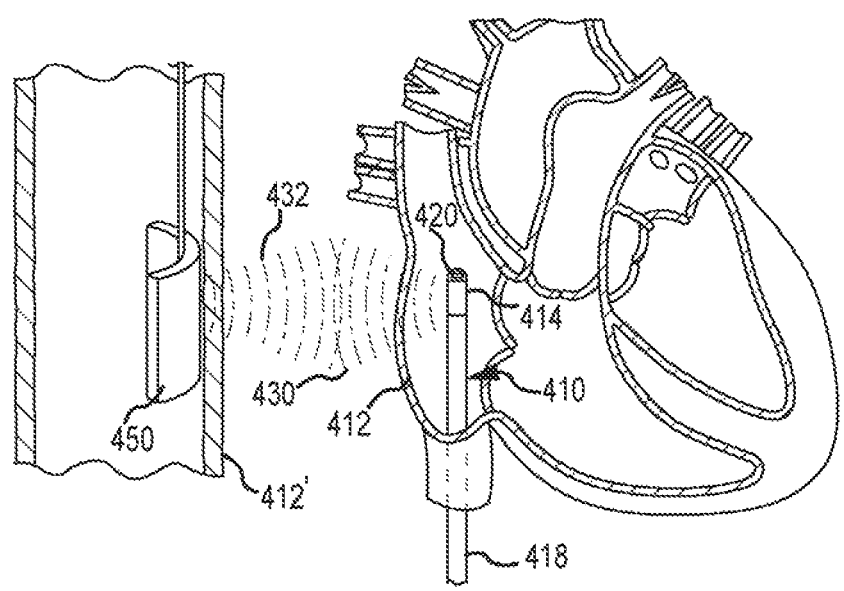
FIG. 8 is a cross-sectional view of a portion of another exemplary catheter with an acoustic transducer.

FIG. 5*d* shows a waveform 53 wherein the return signal (or "echo") is offset by exactly 180 degrees and thereby cancels the emitted pulse (or "ping"). Acoustic waves cancel one another when the emitted waveform is exactly 180 degrees out of phase with the echoing waveform. Canceling the acoustic signal can be useful for a variety of reasons, including mitigating or altogether preventing damage to surrounding tissue and/or focusing the emitted pulse on a particular tissue or within a particular range (e.g., tissue depth) while sparing surrounding tissue. Other exemplary embodiments for canceling the acoustic signal are discussed in more detail below with reference to FIG. 7 and FIG. 8, wherein a shielding device is used. It is noted, however, that the shielding devices described with reference to FIG. 7 and FIG. 8 are not the only ways to achieve a canceling effect. Other methods for achieving a canceling effect may include, but are not limited to, adjusting the frequency or timing of the emitted signal in a known environment such that the return signal will be reflected in such a manner as to result in a canceled signal at predetermined distance from the emitted signal.

In addition to the canceling effect, a wide band of frequencies, amplitudes, phase shifts, and timing may also be implemented to affect various acoustic properties for a wide variety of purposes. For example, different types of tissues have different spectral signatures in terms of amplitude and phase. These spectral signatures can be compiled for different frequencies and this "library" implemented to determine which frequency is most effective for the desired end-use.

As just mentioned with reference to the waveform diagrams shown in FIGS. 5*a*-*d*, the signal strength (e.g., amplitude) from the acoustic transducer can be proportional to the distance of the catheter from the target tissue 12, and therefore can be used to determine if the catheter is in good contact with a tissue (e.g., the myocardium). Signal strength (as observed by the peaks in waveform) may also indicate a level of contact between the catheter and moving tissue. For example, a strong signal may indicate that the catheter is in good contact with the moving heart wall. If the signal strength is weak, this may indicate that the catheter was removed from contact with the moving heart wall.

In addition, the processed signals can be used for dynamic contact assessment for moving tissue 12. That is, electrical signals are generated by the acoustic transducer 20 in response to movement of the catheter shaft 18. For example, as mentioned above, if the catheter shaft 18 is not in contact with the moving target tissue 12, or is in contact with stationary tissue, acoustic feedback may not correlate well with the corresponding heartbeat signal. On the other hand, a strong correlation between the heartbeat signal and output by the acoustic transducer 20 indicates that the catheter shaft 18 is in good contact with the moving target tissue 12.

Signal periodicity is also a strong indicator of dynamic contact assessment. For example, if the period between heartbeats corresponds well with the period between output by the acoustic transducer, this correlation may indicate that the catheter is moving in response to the heartbeat. Therefore, the user is able to use this indicator for assessing the level of contact between the catheter and the moving heart wall, e.g., for an ablation procedure. The user may also assess the level of contact between the catheter 10 and the moving heart wall 12. In an exemplary embodiment, higher amplitude output indicates more contact, and lower amplitude indicates less contact. The user can use this feedback to increase or decrease contact of the catheter 18 with the moving heart wall 12 to achieve the desired contact.

Before continuing, it is noted that although the waveforms shown in FIGS. 5*a*-*d* are output on a device such as can be used for monitoring a patient's heartbeat, the present invention is not limited to use with any particular type of output device. Any suitable analog and/or digital device can be implemented for indicating electrode-tissue contact to a user. In another exemplary embodiment, the electrical signals generated by acoustic transducer 20 can be further characterized using a suitable processing device such as, but not limited to, a desktop or laptop computer. Such processing device can be implemented to receive the voltage signal generated by the acoustic transducer and convert it to a corresponding contact condition for the catheter 10 and output for the user, e.g., at a display device.

Figure 6:
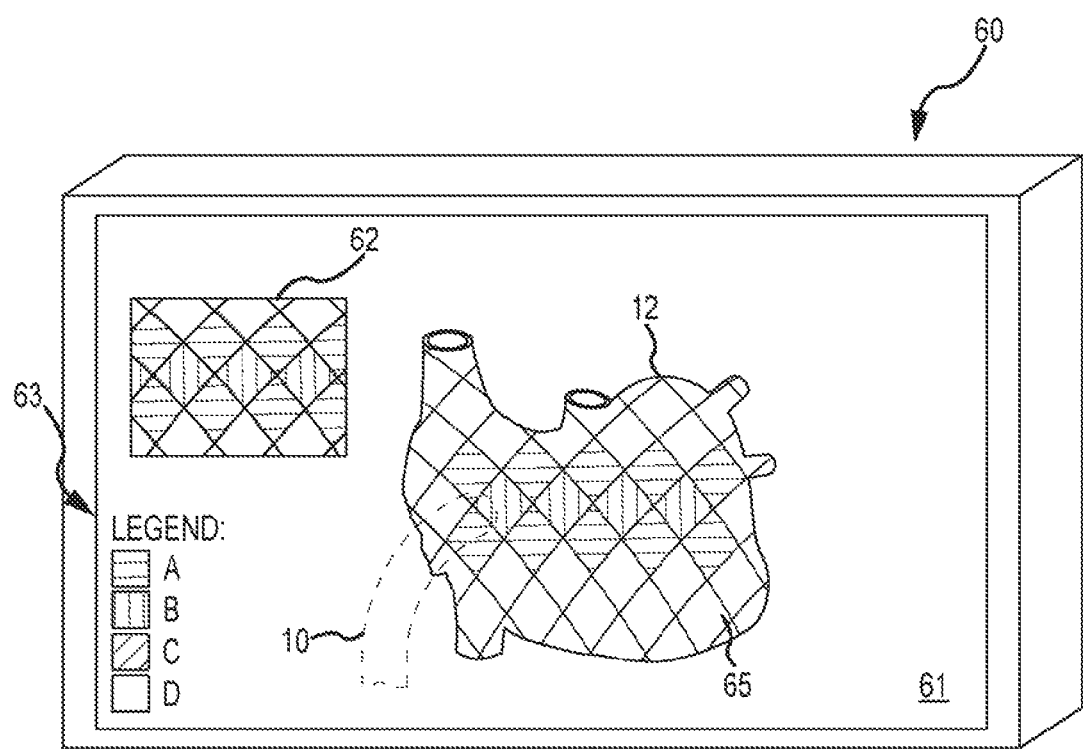
FIG. 6 shows exemplary output from an acoustic transducer which has been further characterized using imaging techniques to provide the user with a visual model of the patient's heart and the catheter location relative thereto.

FIG. 6 shows exemplary output from an acoustic transducer 20 which has been further characterized using imaging techniques to provide the user with a visual model of the patient's heart 12 and the catheter 10 location relative thereto. The output device 60 may include any suitable display 61, wherein a model image of the tissue 12 can be displayed for a user.

In an exemplary embodiment, the model image may include a matrix 65 shown superimposed on the tissue 12. The matrix 65 may indicate target areas on the tissue 12. The user may also be able to "zoom in," as shown by inset 62 on the display 61. Each block in the matrix can be color-coded (or otherwise coded) to indicate tissue assessment. For example, the blocks are shown in FIG. 6 with varying degrees of cross-hatching to indicate different tissue properties. A legend 63 can be provided for the user to aid in interpreting the tissue properties. For example, the color-coding or cross-hatching may indicate one or more of the following tissue assessments: tissue contact, lesion formation, tissue temperature, pressure, etc.

Of course the output device is not limited to a display device. For example, the electrode-tissue contact can be output to the user as an audio or tactile feedback (e.g., vibrations) on the handle of the catheter. Circuitry for conveying output of the acoustic transducer to a user in one form or another can be readily provided by those having ordinary skill in the electronics arts after becoming familiar with the teachings herein.

FIG. 7 is a cross-sectional view of a portion of another exemplary catheter 310 with an acoustic transducer 320. It is noted that 300-series reference numbers are used in FIG. 7 to refer to like elements described above. Therefore the description of some elements may not be repeated in the discussion of FIG. 7.

Catheter 310 may comprise a flexible catheter shaft 318 with at least one acoustic transducer 320. The acoustic transducer 320 is oriented such that the output signal is substantially parallel to the central axis of the catheter shaft 318 such that the transducer can be used to assess contact, and is responsive to movement or deflection, for the distal end portion 314 of the catheter 310.

In this embodiment, an acoustic reflector or shielding device 350 can be provided to reflect acoustic waves and effectively cancel the signal at a predetermined distance from the output acoustic signals, e.g., as illustrated by the waveform diagram in FIG. 5d. For example, the shielding device 350 can be a cylindrical shield that can be inserted into the patient's esophagus 312'. The emitted acoustic energy can be timed such that acoustic waves being reflected from the shielding device 350 cancel the emitted acoustic waves at a desired distance sufficient to reduce or altogether prevent acoustic energy being absorbed by tissue outside of the heart (e.g., by the esophagus 312').

FIG. 8 is a cross-sectional view of a portion of another exemplary catheter 410 with an acoustic transducer 420. It is noted that 400-series reference numbers are used in FIG. 8 to refer to like elements described above. Therefore the description of some elements may not be repeated in the discussion of FIG. 8.

Catheter 410 may comprise a flexible catheter shaft 418 with at least one acoustic transducer 420. The acoustic transducer 420 is oriented such that the output signal is substantially parallel to the central axis of the catheter shaft 418 such that the transducer can be used to assess contact, and is responsive to movement or deflection, for the distal end portion 414 of the catheter 410.

In this embodiment, a separate shielding device 450 can be provided to reflect acoustic waves and effectively cancel the signal at a predetermined distance from the output acoustic signals, e.g., as illustrated by the waveform diagram in FIG. 5d. For example, the shielding device 450 can be a semi-cylindrical shield or "curved spatula" that can be inserted into the patient's esophagus. Alternatively, where an open-chest procedure is being performed, the shielding device 450 can be inserted via MIS to a location external to the esophagus (or other part of the patient's body which the user desires to shield from the acoustic energy being emitting).

As already described above, emitted acoustic energy can be timed such that acoustic waves being reflected from the shielding device 450 cancel the emitted acoustic waves at a desired distance sufficient to reduce or altogether prevent acoustic energy being absorbed by tissue outside of the heart (e.g., by the esophagus).

Examples

The following are examples of other embodiments which are contemplated, and are provided for purposes of illustration, but are not intended to be limiting in any manner.

A method comprising: emitting acoustic signals from a catheter; receiving reflected acoustic signals at the catheter; and assessing a tissue based on the received acoustic signals.

The method, further comprising determining a level of contact between the catheter and the tissue based on the acoustic signals.

The method, further comprising reducing noise artifacts.

The method, further comprising simultaneously emitting and receiving the acoustic signals.

The method, further comprising alternating emitting and receiving the acoustic signals.

The method, further comprising generating a canceling effect of acoustic energy at a desired distance to reduce or eliminate damage to surrounding tissue or anatomical structures.

The method, further comprising assessing contact of the catheter with the tissue.

The method, further comprising assessing tissue properties including: tissue depth, tissue layers, tissue interfaces, and tissue type.

The method, further comprising outputting acoustic energy for lesion formation.

The method, further comprising generating acoustic energy for lesion formation at a predetermined tissue depth.

The method, further comprising reflecting acoustic energy from a shielding device to generate a canceling effect of acoustic energy at a desired distance to reduce or eliminate damage to surrounding tissue or anatomical structures.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. It is intended that all matter contained in the above description or shown in the accompanying drawings shall be interpreted as illustrative only and not limiting. Changes in detail or structure can be made without departing from the spirit of the invention as defined in the appended claims.

What is claimed is:

1. An acoustic assessment system for a catheter, the system comprising:
   a flexible catheter shaft;
   at least one acoustic transducer coupled to the flexible catheter shaft, the at least one acoustic transducer configured to emit a generated acoustic signal for reflection by an adjacent tissue, the at least one acoustic transducer configured to receive a reflected acoustic signal from the adjacent tissue responsive to the emitted acoustic signal;
   an output device electrically connected to the at least one acoustic transducer, the output device including a processing device configured to interpret electrical signals generated in response to the reflected acoustic signal and corresponding to one or more property of the tissue, wherein the processing device is configured to interpret an in-phase reflected acoustic signal as the flexible catheter shaft is in an endoluminal flow environment and an out-of-phase reflected acoustic signal as indicating the flexible catheter shaft is in contact with the adjacent tissue;

a window positioned adjacent to the at least one acoustic transducer, the window configured to focus the generated acoustic signal; and wherein the output device is configured to generate output for assessing one or more properties of the tissue.

2. The system of claim 1, wherein the at least one acoustic transducer includes separate emitters and receivers.

3. The system of claim 1, wherein the at least one acoustic transducer includes combination emitters/receivers.

4. The system of claim 1, wherein a level of contact between a distal portion of the flexible catheter shaft and the tissue corresponds to the electrical signals generated by the at least one acoustic transducer in response to the reflected acoustic signal.

5. The system of claim 1, wherein a level of contact is proportional to at least one of the following: signal strength, amplitude of the electrical signals, and periodicity of the electrical signals.

6. The system of claim 1, further comprising a compliant layer at least partially surrounding the at least one acoustic transducer, the compliant layer configured to reduce noise effects from intermittent contact of the distal portion.

7. The system of claim 1, further comprising an ablative element coupled to the flexible catheter shaft and wherein the at least one acoustic transducer is housed one of on a lateral surface, on a tip portion, within a distal portion of the flexible catheter shaft and is one of spaced from, abutting, and integrated into the ablative element.

8. The system of claim 1, wherein the at least one acoustic transducer is provided on an outer surface of a distal portion of the flexible catheter shaft.

9. The system of claim 1, wherein the at least one acoustic transducer includes an acoustic film.

10. The system of claim 1, wherein the at least one acoustic transducer includes a plurality of acoustic transducer elements, and wherein the plurality of acoustic transducer elements are configured as one of the following: a one-dimension array, a two-dimension array, a three-dimensional array, a geometric shape, a sphere, and a cylinder.

11. The system of claim 1, wherein the at least one acoustic transducer and the processing device are configured to generate a canceling effect of acoustic energy at a desired distance to reduce or eliminate damage to surrounding tissue or anatomical structures during operation of the at least one transducer.

12. The system of claim 1, wherein the at least one acoustic transducer is configured to generate acoustic energy for assessing contact of the catheter with the tissue.

13. The system of claim 1, wherein the output device is configured to generate output indicating tissue depth, tissue layers, tissue interfaces, and tissue type.

14. The system of claim 1, wherein the at least one acoustic transducer is configured to generate acoustic energy for lesion formation.

15. The system of claim 1, further comprising a shielding device positionable adjacent an anatomical structure, the shielding device causing a canceling effect of acoustic energy at a desired distance to reduce or eliminate damage to surrounding tissue or anatomical structures.

16. A system for assessing catheter-tissue contact, the system comprising:

means for emitting acoustic signals from a catheter for reflection by an adjacent tissue, the means for emitting acoustic signals arranged in a two-dimensional arrangement;

means for receiving reflected acoustic signals at the catheter generated in response to the emitted acoustic signals reflected against the tissue;

means for comparing phases of the emitted and received acoustic signals to determine whether a flexible shaft of the catheter is in an endoluminal flow environment, wherein in-phase reflected acoustic signals indicate the flexible catheter shaft is in the endoluminal flow environment and out-of-phase reflected acoustic signals indicate the flexible catheter shaft is in contact with the adjacent tissue;

means for assessing contact of the catheter with the tissue; and means for outputting data for assessing tissue properties of the tissue based on the received acoustic signals, the tissue properties associated with tissue depth, tissue layers, tissue interfaces, and tissue type.

17. The system of claim 16, further comprising means for generating a canceling effect of acoustic energy at a desired distance to reduce or eliminate damage to surrounding tissue or anatomical structures.

18. The system of claim 16, wherein the means for assessing tissue properties further includes at least one of: ablation lesion depth, ablation lesion volume, and continuity of an ablation lesion.

19. The system of claim 16, further comprising means for generating acoustic energy for lesion formation at a predetermined tissue depth.

20. An acoustic assessment system for a catheter, the system comprising:

a catheter shaft;

at least one acoustic transducer coupled to the catheter shaft;

a window positioned adjacent to the at least one acoustic transducer, the window configured to focus the generated acoustic signal; and an output device electrically connected to the at least one acoustic transducer, the output device including a processing device configured to generate output for assessing properties of adjacent tissue, the processing device configured to:

compare a generated acoustic signal emitted by the at least one acoustic transducer to a reflected acoustic signal received in response to the generated acoustic signal;

determine a phase relation associated with the generated acoustic signal and the reflected acoustic signal;

identify an in-phase reflected acoustic signal indicating the catheter shaft is in an endoluminal flow environment, or an out-of-phase reflected acoustic signal indicating the catheter shaft is in contact with the tissue; and assess properties of the tissue including tissue depth, tissue layers, tissue interfaces, and tissue type, based on the reflected acoustic signal.

* * * * *